US012672912B2

(12) United States Patent　　　　　　　(10) Patent No.: US 12,672,912 B2
Highsmith et al.　　　　　　　　　　　(45) Date of Patent:　　　Jul. 7, 2026

(54) CATHETER FOR ENDOVASCULAR SYMPATHETIC DENERVATION OF SPASMED INTRACRANIAL ARTERIES

(71) Applicant: Biosense Webster (Israel) Ltd., Yokneam (IL)

(72) Inventors: Debby E. Highsmith, Laguna Niguel, CA (US); Ariel Garcia, Vista, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/892,759

(22) Filed: Jun. 4, 2020

(65) Prior Publication Data

US 2021/0015550 A1　　　Jan. 21, 2021

Related U.S. Application Data

(60) Provisional application No. 62/875,070, filed on Jul. 17, 2019.

(51) Int. Cl.
　　A61B 18/14　　　(2006.01)
　　A61B 18/00　　　(2006.01)
(52) U.S. Cl.
　　CPC .. A61B 18/1492 (2013.01); A61B 2018/0016 (2013.01); A61B 2018/00577 (2013.01);
　　　　　　　　(Continued)
(58) Field of Classification Search
　　None
　　See application file for complete search history.

(56) References Cited

U.S. PATENT DOCUMENTS 6,221,071 B1　　4/2001　Sherry et al.
7,344,533 B2　　3/2008　Pearson et al.
　　　　　　(Continued)

FOREIGN PATENT DOCUMENTS

CN　　106456247 A　　2/2017
EP　　2 641 556 A1　　9/2013
　　　　　(Continued)

OTHER PUBLICATIONS

U.S. Appl. No. 62/875,070, filed Jul. 17, 2019 by Highsmith et al., entitled: "Catheter for Endovascular Sympathetic Denervation of Spasmed Intracranial Arteries."

(Continued)

*Primary Examiner* — Joanne M Rodden
*Assistant Examiner* — Nora W Rhodes
(74) *Attorney, Agent, or Firm* — FBT Gibbons LLP

(57)　　　　　ABSTRACT

An apparatus includes a catheter assembly having a catheter with a catheter body and an end effector connected with a distal end of the catheter. The catheter assembly optionally includes an outer sheath or introducer tool. The end effector includes a spine assembly having a plurality of spines. An electrode is associated with each spine of the spine assembly. The electrodes are longitudinally staggered along their respective spines. The spines extend outward from a longitudinal axis of the catheter body such that the spine define a circular arrangement. This arrangement with the longitudinally spaced electrodes defines a helical array such that an elongated circumferential ablation pattern is achieved.

18 Claims, 10 Drawing Sheets

(52) U.S. Cl.
CPC ............... *A61B 2018/00797* (2013.01); *A61B 2018/1435* (2013.01)

(56) References Cited

U.S. PATENT DOCUMENTS

| | | | |
|---|---|---|---|
| 8,287,531 B2 | 10/2012 | Mest | |
| 8,979,839 B2 | 3/2015 | De La Rama et al. | |
| 9,314,299 B2 | 4/2016 | Fang | |
| 9,439,722 B2 | 9/2016 | Grunewald et al. | |
| 10,362,952 B2 | 7/2019 | Basu et al. | |
| 10,537,286 B2 | 1/2020 | Diep et al. | |
| 12,256,984 B2 | 3/2025 | Ku et al. | |
| 2001/0016739 A1 | 8/2001 | Goldman et al. | |
| 2010/0076426 A1* | 3/2010 | de la Rama | A61B 5/0036 |
| | | | 606/41 |
| 2012/0116392 A1* | 5/2012 | Willard | A61B 18/1492 |
| | | | 606/41 |
| 2012/0271140 A1* | 10/2012 | Kordis | A61B 5/283 |
| | | | 600/375 |
| 2012/0296232 A1* | 11/2012 | Ng | A61B 18/1492 |
| | | | 600/554 |
| 2013/0231659 A1* | 9/2013 | Hill | A61B 18/1492 |
| | | | 606/41 |
| 2013/0253504 A1* | 9/2013 | Fang | A61B 5/4848 |
| | | | 606/41 |
| 2013/0304047 A1* | 11/2013 | Grunewald | A61B 18/1492 |
| | | | 606/1 |
| 2014/0018788 A1* | 1/2014 | Engelman | A61B 18/1492 |
| | | | 606/33 |
| 2015/0038961 A1* | 2/2015 | Clark | A61B 18/1492 |
| | | | 606/41 |
| 2015/0141982 A1* | 5/2015 | Lee | A61B 5/287 |
| | | | 606/41 |
| 2017/0100189 A1 | 4/2017 | Clark et al. | |
| 2017/0165000 A1* | 6/2017 | Basu | A61B 18/1492 |
| 2018/0192958 A1 | 7/2018 | Wu | |
| 2018/0360534 A1* | 12/2018 | Teplitsky | A61B 5/02055 |
| 2018/0368914 A1* | 12/2018 | Cheng | A61L 29/08 |

FOREIGN PATENT DOCUMENTS

| | | | |
|---|---|---|---|
| EP | 2 662 048 A2 | 11/2013 | |
| EP | 2752153 A1 | 7/2014 | |
| EP | 3 178 516 A1 | 6/2017 | |
| WO | WO 2012/058434 A1 | 5/2012 | |
| WO | WO 2014/008489 A1 | 1/2014 | |

OTHER PUBLICATIONS

International Search Report and Written Opinion dated Dec. 8, 2020, for International Application No. PCT/ US2020/041363, 16 pages.
PCT International Preliminary Report on Patentability issued Jan. 18, 2022 in International Application No. PCT/US2020/041363, 8 pages.
Chinese Office Action dated Mar. 20, 2024 for Application No. 202080051649.X, 13 pages.
Chinese Office Action dated Jun. 14, 2024 for Application No. 202080051649.X, 7 pages.
Chinese Office Action dated Sep. 23, 2024 for Application No. 202080051649.X, 15 pages.
Chinese Office Action dated Dec. 19, 2024 for Application No. 202080051649.X, 10 pages.
Chinese Office Action dated Feb. 25, 2025 for Application No. 202080051649.X, 11 pages.
Japanese Office Action dated Feb. 13, 2024 for Application No. 2022-502478, 18 pages.
Japanese Office Action dated May 20, 2024 for Application No. 2022-502478, 24 pages.
European Examination Report dated Mar. 24, 2025 for EP Application No. 20750937.3, 5 pages.

\* cited by examiner

CATHETER FOR ENDOVASCULAR SYMPATHETIC DENERVATION OF SPASMED INTRACRANIAL ARTERIES

PRIORITY

This application claims priority to U.S. Provisional Patent Application Ser. No. 62/875,070, filed Jul. 17, 2019, entitled "Catheter for Endovascular Sympathetic Denervation of Spasmed Intracranial Arteries," the disclosure of which is incorporated by reference herein.

BACKGROUND

In certain circumstances, treatment of a subject may be performed with a procedure that ablates tissue of a subject to modify the behavior or other properties of that tissue. In some circumstances where the subject presents a spasmed intracranial artery, ablation may be used to produced sympathetic denervation of the spasmed intracranial artery. Such ablation procedures may include the use of catheters that are configured for endovascular use. These catheters may be configured to provide precise and controlled ablation in such manners as may be desired.

While several catheters have been made and used, it is believed that no one prior to the inventors has made or used the invention described, illustrated, and claimed herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
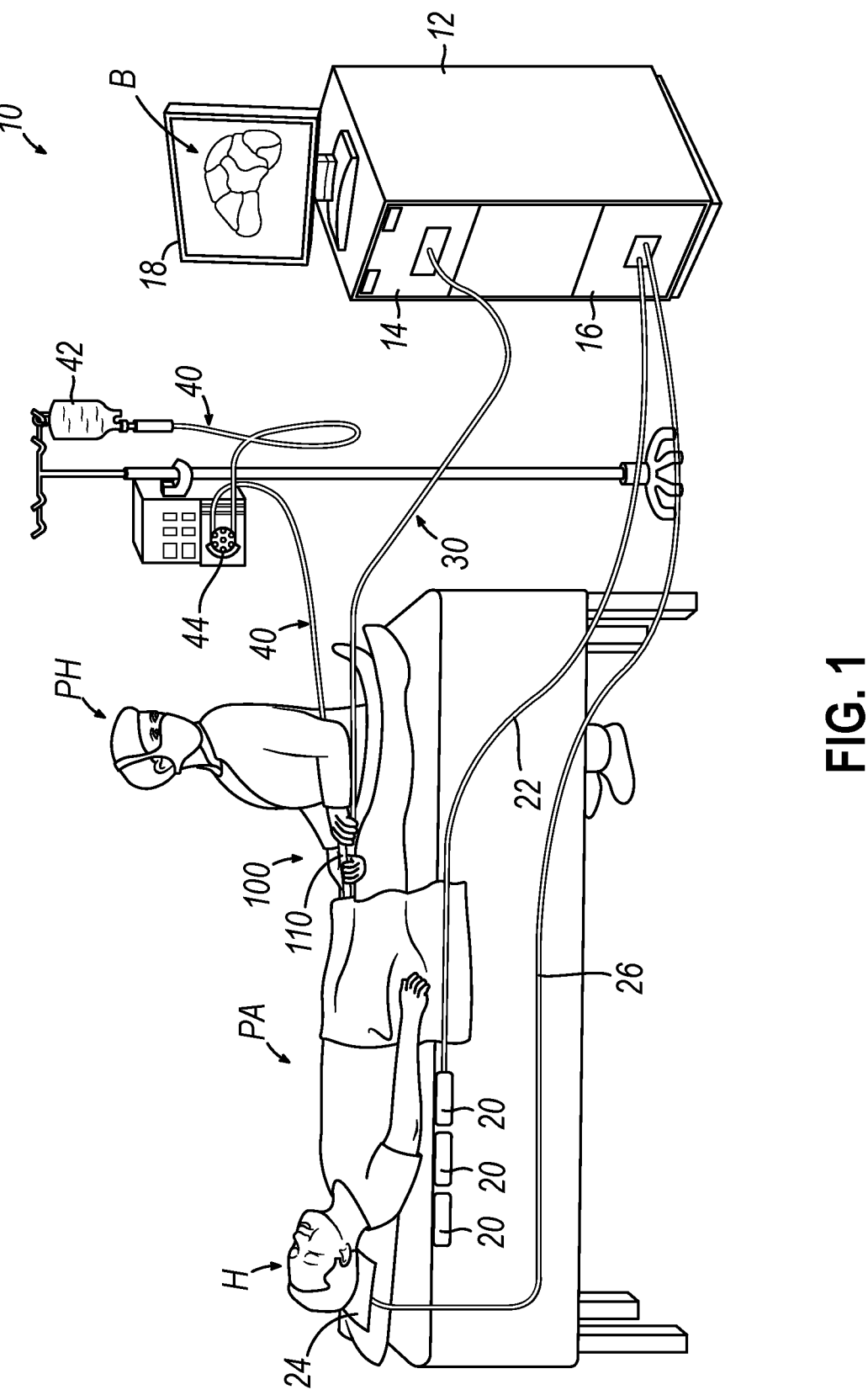
FIG. 1 depicts a schematic view of a medical procedure in which a catheter of a catheter assembly is inserted in a patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. OVERVIEW OF EXEMPLARY CATHETER SYSTEM

FIG. 1 shows an exemplary medical procedure and associated components of an intracranial ablation system. In particular, FIG. 1 shows a physician (PH) grasping a handle (110) of a catheter assembly (100). Catheter assembly (100) includes an end effector of a flexible catheter (120) as will be described further below. Catheter (120) is disposed in a patient (PA) to ablate a spasmed intracranial artery in a brain (B) of patient (PA). Catheter assembly (100) is coupled with a guidance and drive system (10) via a cable (30). Catheter assembly (100) is also coupled with a fluid source (42) via a fluid conduit (40), though this is merely optional. A set of field generators (20) are positioned underneath patient (PA) and are also coupled with guidance and drive system (10) via a cable (22). A ground pad (24) is positioned underneath a head (H) of patient (PA) and connects with guidance and drive system (10) via a cable (26).

Guidance and drive system (10) of the present example includes a console (12) and a display (18). Console (12) includes a first driver module (14) and a second driver module (16). First driver module (14) is coupled with catheter assembly (100) via cable (30). First driver module (14) is operable to provide RF power to electrodes of the end effector to thereby ablate tissue. Various examples of configurations for such electrodes will be described in greater detail below. Such electrodes may be operable to apply monopolar RF energy to tissue or bipolar RF energy to tissue. In some versions, first driver module (14) is also operable to receive position indicative signals from one or more position sensors in the end effector. In such versions, a processor (not shown) of console (12) is operable to process the position indicative signals from the position sensors to thereby determine the position of the end effector of catheter (120) within patient (PA).

Second driver module (16) is coupled with field generators (20) via cable (22) and ground pad (24) via cable (26). In other versions, ground pad (24) and cable (26) may be coupled with and controlled by first driver module (14). Second driver module (16) is operable to activate field generators (20) to generate an alternating magnetic field around the head (H) and brain (B) of patient (PA). For instance, field generators (20) may include coils that generate alternating magnetic fields in a predetermined working volume that contains brain (B) within head (H) of patient (PA).

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from position sensors of the end effector as will be described further below. For instance, as the end effector of catheter (120) moves within patient (PA), the corresponding position data from the position sensors may cause the processor of console (12) to update the patient anatomy views in display (18) in real time to depict the regions of patient anatomy around the end effector as the end effector moves within patient (PA). Moreover, the processor of console (12) may drive display (18) to show locations of spasmed tissue sites, as detected by preoperatively or intraoperatively obtained images or detected by other sensing means of the end effector. By way of example only, the processor of console (12) may drive display (18) to superimpose the locations of spasmed tissue sites on the images of the patient's anatomy, such as by superimposing an illuminated dot, a crosshair, or some other form of visual indication of spasmed tissue sites.

The processor of console (12) may also drive display (18) to superimpose the current location of the end effector on the images of the patient's anatomy, such as by superimposing an illuminated dot, a crosshair, a graphical representation of the end effector, or some other form of visual indication. Such a superimposed visual indication may also move within the images of the patient anatomy on display (18) in real time as physician (PH) moves the end effector within patient (PA), thereby providing real-time visual feedback to the operator about the position of the end effector within patient (PA) or subject as the end effector moves within patient (PA). The images provided through display (18) may thus effectively provide a video tracking the position of the end effector within patient (PA), without necessarily having any optical instrumentation (i.e., cameras) viewing the end effector. In the same view, display (18) may simultaneously visually indicate the locations of spasmed tissue sites as mentioned above. Physician (PH) may thus view display (18) to observe the real time positioning of the end effector in relation to the spasmed tissue sites and in relation to images of the adjacent anatomical structures in patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). In some variations, conduit (40), fluid source (42), and pump (44) are omitted entirely. In versions where these components are included, the end effector may be configured to communicate irrigation fluid from fluid source (42) to the target site in patient (PA) as will be described further below. Such irrigation may be provided in any suitable fashion as will be apparent to those skilled in the art in view of the teachings herein.

II. EXEMPLARY CATHETER END EFFECTOR WITH STAGGERED FREE ENDS

Figure 2:
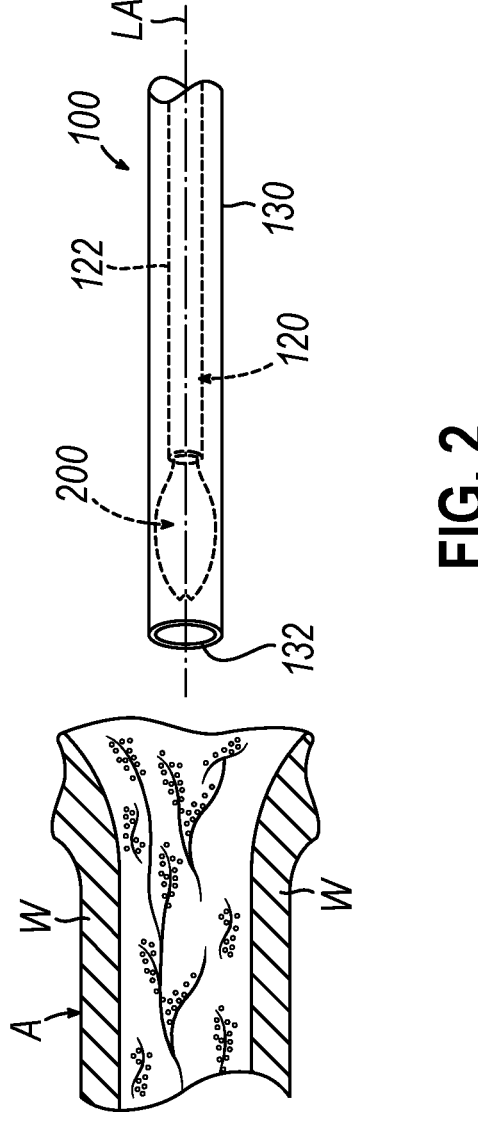
FIG. 2 depicts a side view of an exemplary catheter assembly including an exemplary introducer tool and exemplary catheter usable with the introducer tool, with the catheter assembly approaching an artery of the subject of FIG. 1.

FIG. 2 depicts portions of catheter assembly (100) adjacent to an exemplary tissue structure in the form of an artery (A), which is shown in cross-section. Artery (A) is a tubular structure having a sidewall (W). As shown, catheter (120) is positioned within an introducer tool (130) having an open end (132). Catheter (120) includes a catheter body (122) and end effector (200). Catheter body (122) defines a longitudinal axis (LA), which extends from a proximal end to a distal end of catheter assembly (100). Catheter assembly (100), with catheter (120) positioned within introducer tool (130), can be guided within artery (A) to a desired location nearby where ablation may be applied. As shown in FIG. 2, when end effector (200) of catheter (120) is positioned within introducer tool (130), end effector (200) adopts a contracted state.

Figure 3:
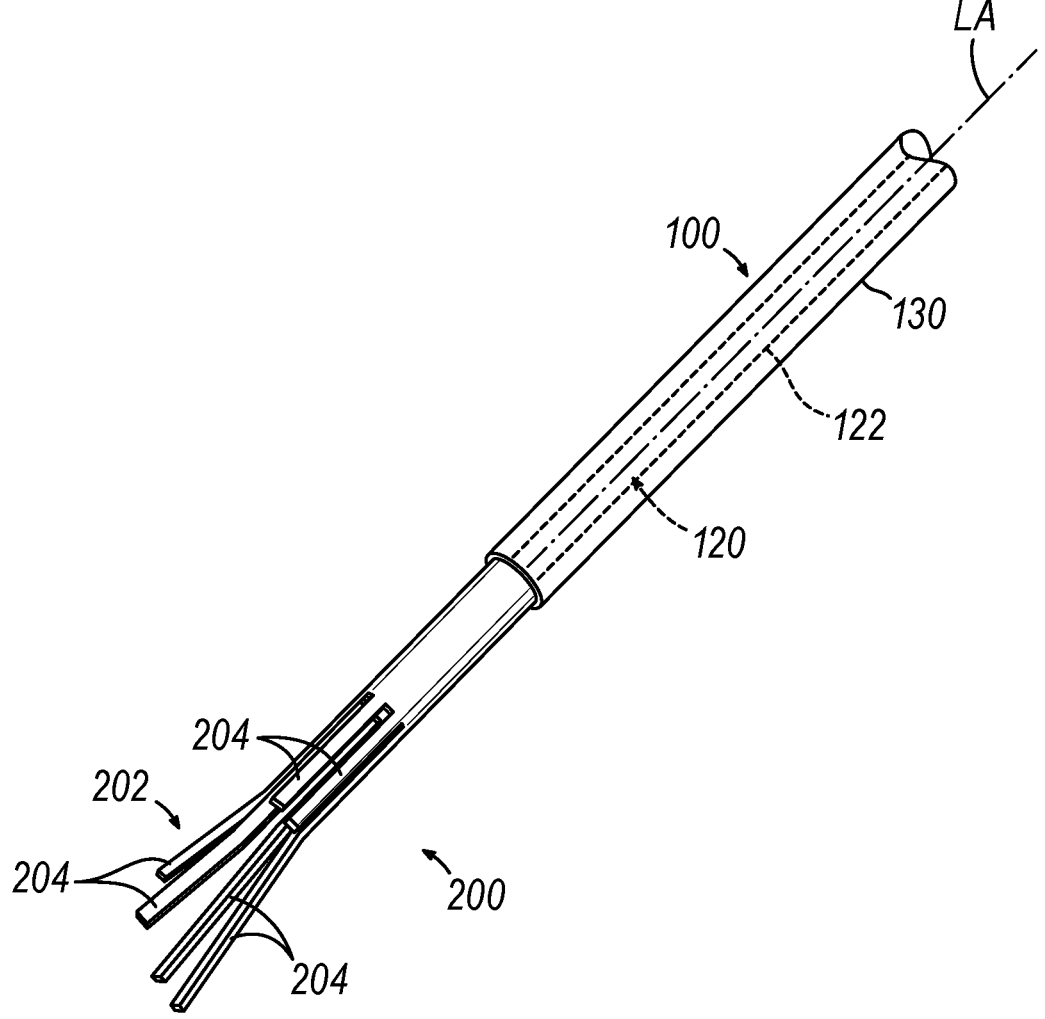
FIG. 3 depicts a perspective view of the catheter assembly of FIG. 2 with an end effector of the catheter extended distal of the introducer tool.

FIG. 3 depicts portions of catheter assembly (100) similar to FIG. 2 but shown with catheter (120) extended distally from introducer tool (130). End effector (200) connects with the distal end of catheter body (122). In this arrangement shown in FIG. 3, end effector (200) of catheter (120) is unbound by introducer tool (130) in contrast to the arrangement shown in FIG. 2. End effector (200) is resiliently biased in the present version to expand outwardly from longitudinal axis (LA) defined by catheter body (122). For instance, when end effector (200) is otherwise unbounded or unconstrained by introducer tool (130), end effector (200) adopts an expanded state. In some versions, the resilient bias of end effector (200) is temperature dependent such that in addition to being unbounded by introducer tool (130), end effector (200) must reach a certain temperature before it will adopt an expanded state as mentioned above. For example, end effector (200) may remain contracted when end effector (200) is at room temperature or about 70 degrees Fahrenheit, while end effector (200) may adopt the expanded state when end effector (200) is at a higher temperature, e.g., above about 85 degrees Fahrenheit, or at body temperature or about 99 degrees Fahrenheit.

End effector (200) includes a spine assembly (202) with a plurality of spines (204). In the illustrated version of FIGS.

3-4B, each spine (204) includes an inflection point or hinge (206) about which a portion of each spine (204) may expand or deflect outwardly from center of end effector (200). However, such an inflection point or hinge (206) is not required in all versions, and in other versions the outward expansion of spines (204) may be more gradual or curved rather than bent. In some versions, end effector (200) or spine assembly (202) may be made from nitinol; however, other materials may be used and will be apparent to those skilled in the art in view of the teachings herein. In the expanded state, portions of spines (204) of end effector (200) are configured to contact interior wall (W) of a tubular vessel such as artery (A) of FIG. 2. This contact allows for end effector (200) to be used with ablation procedures as will be described further below.

Figure 4:
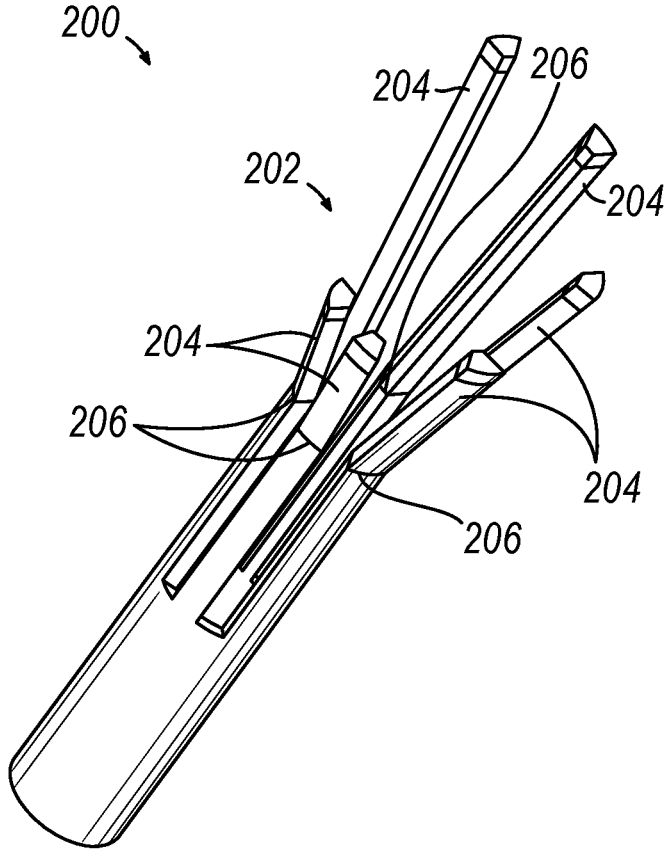
FIG. 4 depicts a perspective view of a distal end of the end effector of the catheter of FIG. 3.
Figure 5:
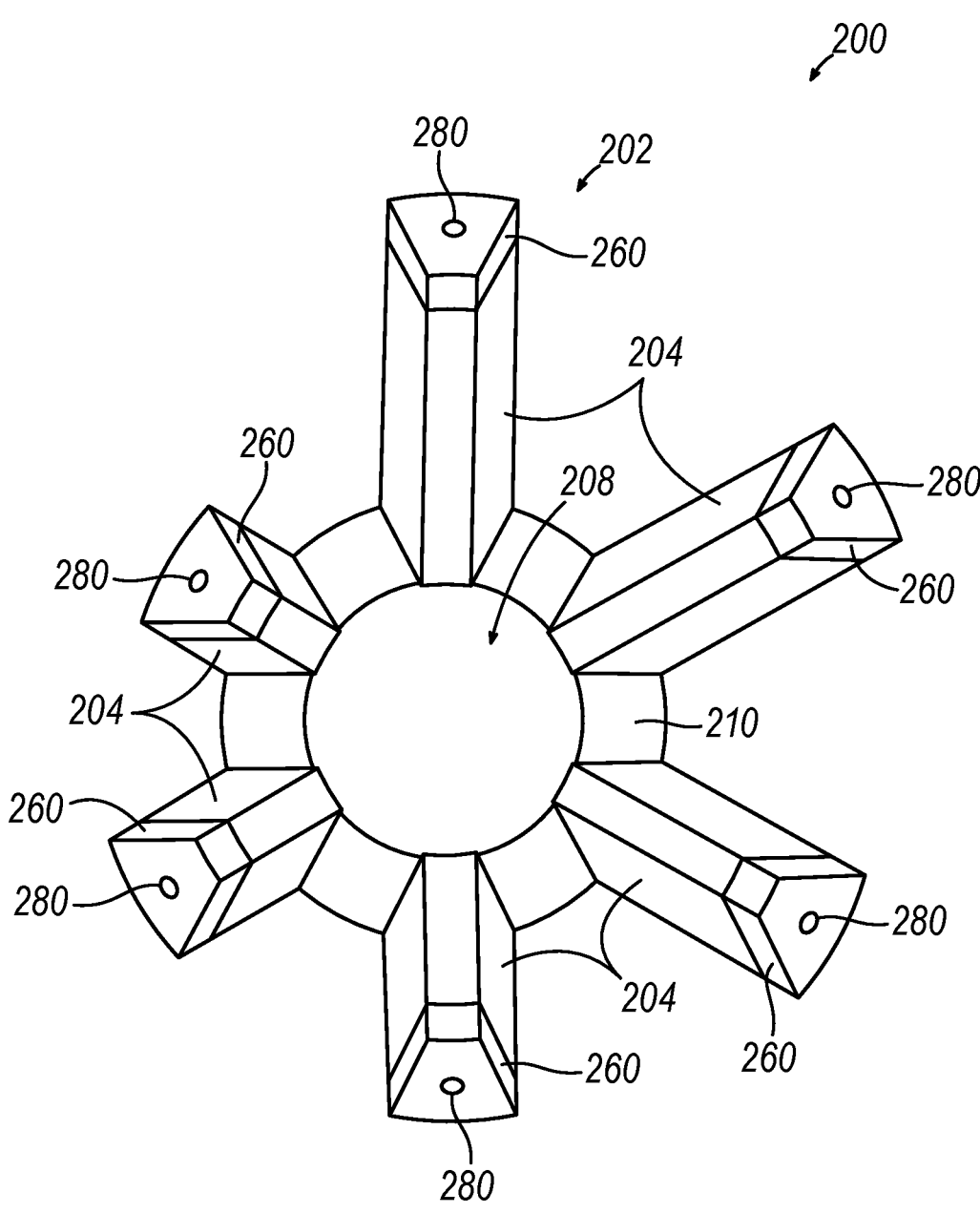
FIG. 5 depicts an end view of the end effector of the catheter of FIG. 3.

Referring to FIGS. 4 and 5, each spine (204) has a distal end, and each spine (204) extends distally with at least two spines (204) extending distally to different lengths. In the illustrated version, but not required in all versions, all spines (204) extend distally to a different length. In one version, each spine (204) extends distally to different lengths in an ascending order. For instance, in one such version spines (204) are located in a circular arrangement and extend distally in an ascending order of length. In this manner, with the exception of the longest spine (204), each other spine (204) of spine assembly (202) will have at least one adjacent spine (204) that extends further distally. The shortest spine (204) will have both adjacent spines (204) extending further distally, while for the longest spine (204) no adjacent spines (204) will extend further distally. In this arrangement, the distal ends of each spine (204) of spine assembly (202) are configured in a helical shape or pattern.

Referring to the illustrated version of FIG. 5, each spine (204) extends from a central apex (208) of spine assembly (202). Central apex (208) is surrounded by a ring (210), and each spine (204) connects with and extends distally from ring (210). In this manner, spines (204) are connected indirectly via ring (210). In other versions, ring (210) may be omitted or replaced with another connecting structure. In a version where ring (210) is omitted, each spine (204) may connect together directly at their respective proximal ends.

Catheter assembly (100) is further configurable to articulate such that end effector (200) can be moved to a position where end effector (200) is deflected away from longitudinal axis (LA). When catheter assembly (100) is not articulated, spine assembly (202) is aligned with catheter body (122) such that central apex (208) is along longitudinal axis (LA). However, when catheter assembly (100) is articulated, central apex (208) of spine assembly (202) is deflected away from longitudinal axis (LA).

As seen in FIG. 5, end effector (200) includes a plurality of electrodes (260). In the illustrated version of FIG. 5, each electrode (260) is connected with a corresponding spine (204) of spines (204). Also in the illustrated version, each electrode (260) is located at the distal end of each respective spine (204). As mentioned above, electrodes (260) are configured to transmit RF energy to ablate tissue. As also mentioned above, some versions of electrodes (260) are configured to apply monopolar RF energy to tissue; while other versions of electrodes (260) are configured to apply bipolar RF energy to tissue.

Figure 6A:
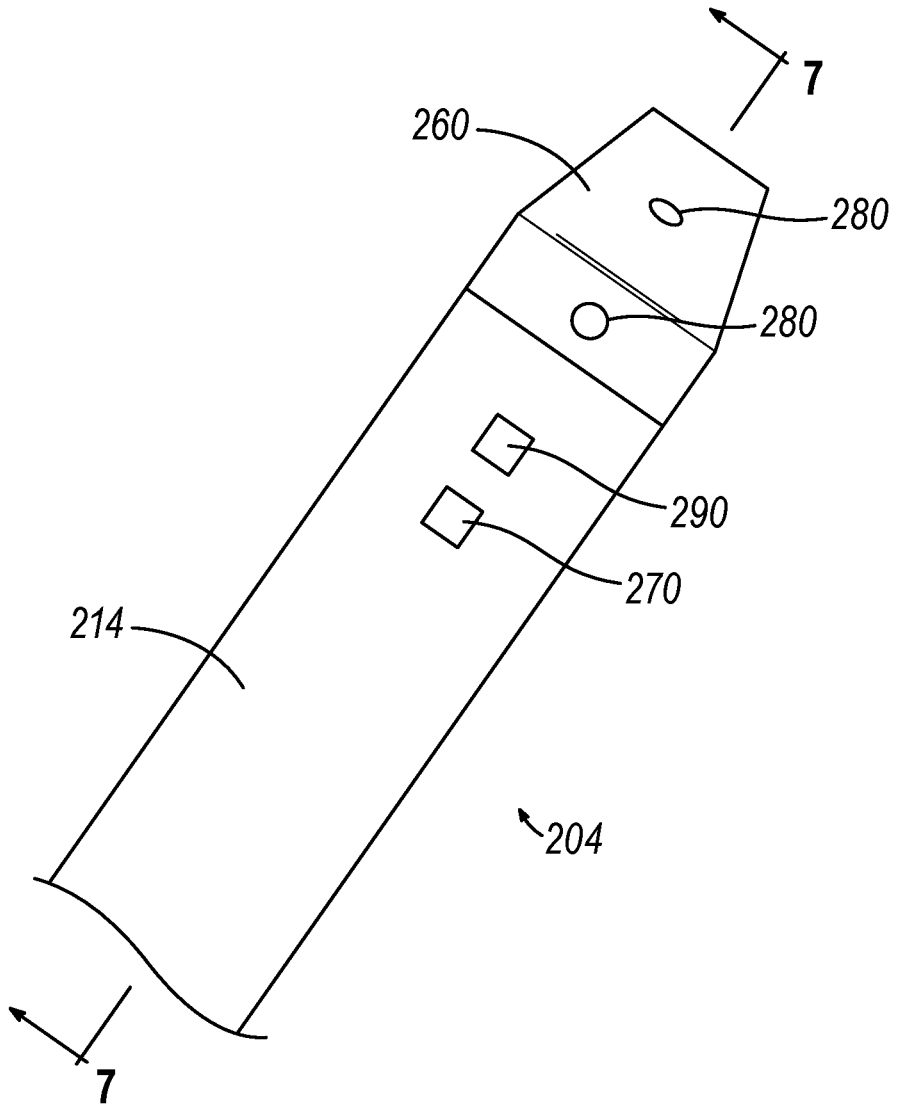
FIG. 6A depicts a perspective view of one of the spines of the end effector of the catheter of FIG. 3, showing an outward facing surface of the spine.
Figure 6B:
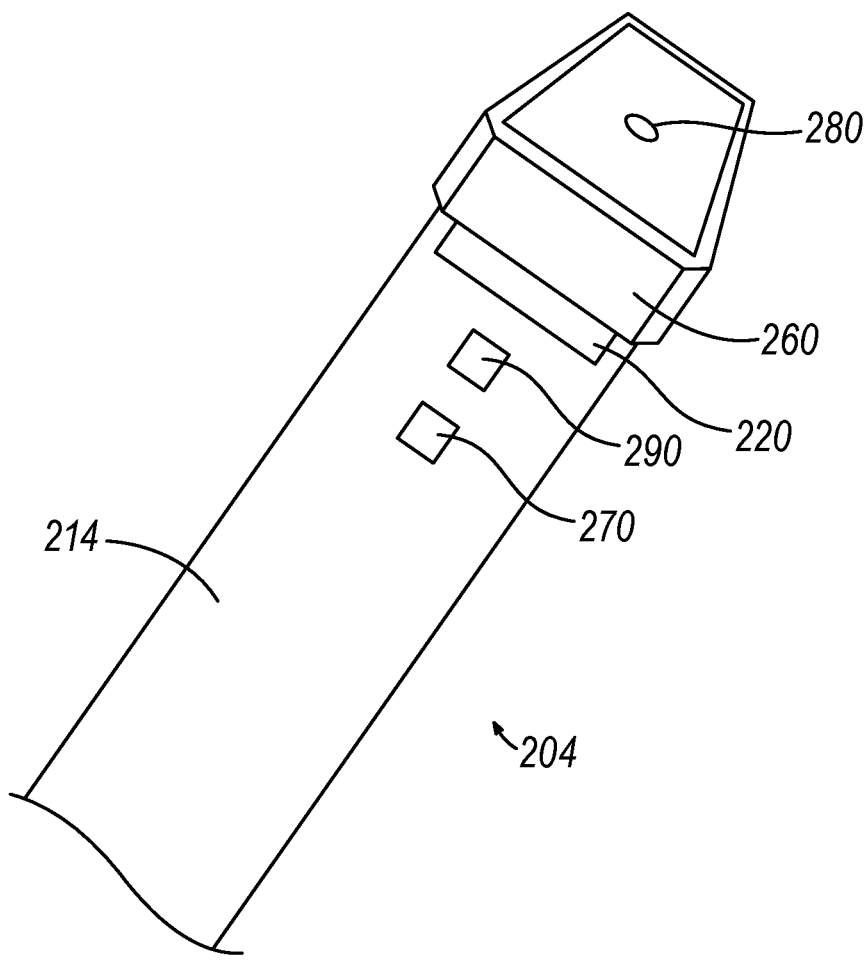
FIG. 6B depicts a perspective view of another exemplary spine usable with the end effector of the catheter of FIG. 3, showing an outward facing surface of the spine.
Figure 7:
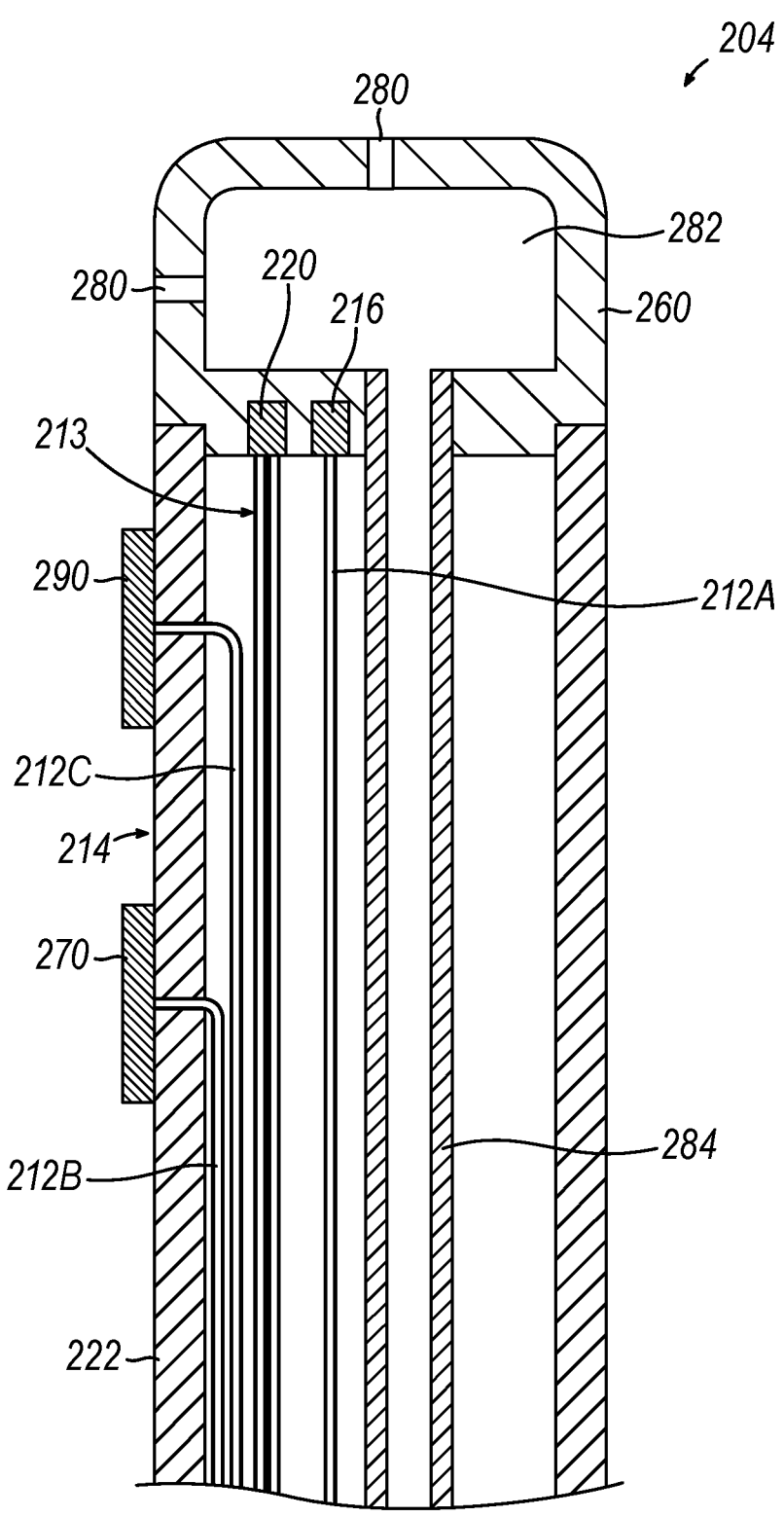
FIG. 7 depicts partial a side view in cross section of the spine of the catheter of FIG. 6A, taken along line 7-7 of FIG. 6A.

Referring to FIG. 7, electrodes (260) of each spine (204) connect with a lead wire (212A) that serves as a conductor configured to transmit RF energy from an energy source to electrode (260). In the illustrated example of FIG. 7, lead wire (212A) transmitting RF energy to electrode (260) connects with electrode (260) at connection (216). Connection (216) can be a terminal connection in some versions, or a soldered connection in other versions. Still other ways to connect lead wire (212A) with electrode (260) will be apparent to those skilled in the art in view of the teachings herein. In the example shown in FIGS. 5, 6A, and 7, electrodes (260) are shown as deep drawn cup electrodes. FIG. 6B depicts spine (204) configured with electrode (260) shown as a ring electrode at the distal end of spine (204). In view of the teachings herein, spines (204) of end effector (200) may be configured with electrodes (260) of any suitable style as will be apparent to those skilled in the art in view of the teachings herein.

As shown and described above, with spines (204) extending distally to different lengths, and with electrodes (260) located at the distal end of each spine (204) of spine assembly (202), catheter (120) has a plurality of electrodes (260) that are longitudinally staggered or spaced. In some versions, the longitudinal spacing of electrodes (260) is irregular such that the spacing between adjacent electrodes (260) varies. The distal ends of spines (204), as described above in at least one version, define a helical shape or pattern. Accordingly, in some versions with this helical shape or pattern and where electrodes (260) are located at the distal ends of each spine (204), catheter (120) has a plurality of electrodes (260) that define a helical array. In this fashion, electrodes (260) create a circumferential ablation in use. In one example catheter (120), the circumferential ablation is achieved over a length from approximately or about 1.0 to approximately or about 1.5 centimeters. Additionally, catheter (120), in some versions, is configured to fit within arteries having diameters from approximately or about 1.5 to approximately or about 1.8 millimeters. By way of example only, and not limitation, a diameter for catheter (120) is approximately or about 1.25 millimeters. In view of the teachings herein, other sizes for catheter (120) and configurations for spines (204) and associated electrodes (260) to achieve other ablation patterns will be apparent to those skilled in the art.

End effector (200) of catheter (120) is further configured with irrigating features (280). For example, as shown in FIGS. 5-6B, exemplary irrigating features (280) are located near the distal end of each spine (204) of end effector (200). FIG. 6A depicts spine (204) having multiple irrigating features (280), with one at the distal-most end and another on an outward facing distal portion of spine (204). Referring to FIG. 7, irrigating features (280) connect with a fluid chamber (282) within a distal end of spine (204). Fluid chamber (282) further connects with an irrigation tube (284) that ultimately is connectable with fluid conduit (40) and fluid source (42) as mentioned above with respect to FIG. 1. As noted above, these irrigation features may be omitted in some versions.

End effector (200) of catheter (120) is further configured with various sensors. Referring to FIGS. 6A-7, each spine (204) of spine assembly (202) includes position sensors (270) and force sensors (290). As mentioned above, position sensors (270) are configured to communicate the position of end effector (200) relative to anatomical features within patient (PA). Force sensors (290) are configured to provide feedback to physician (PH) so that physician (PH) can avoid exceeding forces that may otherwise cause unintended puncture of arteries or other tissues of patient (PA). Referring to FIG. 7, position sensors (270) and force sensors (290) of spines (204) connect with respective lead wires (212B, 212C) within spine (204). Lead wires (212B, 212C) extend through a lumen of catheter (120) and ultimately connect with cable (30), which couples catheter assembly (100) with guidance and drive system (10) as mentioned above. In the present examples of FIGS. 6A and 6B, position sensors (270) and force sensors (290) of spines (204) are located on an outward facing surface (214) of spines (204). However, in other versions, position or force sensors (270, 290) can be located on other surfaces of spines (204).

End effector (200) of catheter (120) also includes temperature sensors (220), where each spine (204) connects with at least one temperature sensor (220). In some versions each temperature sensor (220) is located at the distal end of each respective spine. Also in some versions, each temperature sensor (220) connects with electrode (260) of respective spines (204). For instance, as seen in FIG. 7, temperature sensor (220) is fit within a bore of electrode (260). By way of another example, in FIG. 6B, with a ring style electrode (260), temperature sensor (220) is located along outward facing surface (214) of each spine (204), and adjacent electrode (260) in a contacting arrangement. In either of these configurations, temperature sensor (220) is configured to measure and transmit the temperature at electrode (260). With electrode (260) being configured to contact the artery wall (W) or other tissue, physician (PH) can use temperature sensor (220) to know the temperature that electrode (260) is generating at the ablation site.

In some versions, temperature sensor (220) may include a thermocouple or thermistor. In the depicted embodiment of FIG. 7, a thermocouple is formed by an enameled wire pair (213). One wire of the wire pair is a copper wire, e.g., a number "40" copper wire. The other wire of the wire pair is a constantan wire. These wires of the wire pair are electrically isolated from each other except at their distal ends where they are twisted together, covered with a short thin piece of plastic tubing, e.g., polyamide, and covered with epoxy with good thermal conductive coefficient. The wires extend through the central lumen of the catheter body (122), and then extend out through the control handle (110) and to a connector (not shown) connectable to a temperature monitor (not shown). Alternatively, the temperature sensing means may be a thermistor. A suitable thermistor for use in the present invention is Model No. AB6N2-GC14KA143E/37C sold by Thermometrics (New Jersey). In one version, temperature sensor (220) and electrode (260) are connected by sharing the conductor. In other words, lead wire (212A) connects with electrode (260) and also connects with temperature sensor (220). In this configuration, lead wire (212A) may serve as one of the wires in the pair of wires (213) where temperature sensor (220) is configured as thermocouple for example. Regardless of the form of construction, feedback from temperature sensors (220) may be utilized to provide alerts when sensed temperatures exceed a threshold and/or to automatically modulate the delivery of RF energy during ablation.

Still referring to FIG. 7, spines (204) of end effector (200) are at least partially covered by a nonconductive material (222). In some versions, nonconductive material (222) completely covers spines (204) except for electrode (260). Nonconductive material is a thermoplastic in some instances, and other nonconductive materials that may be used will be apparent to those skilled in the art in view of the teachings herein.

Another feature of catheter (120) is that a proximal end of catheter body (122) has a greater stiffness than the distal end. This allows for positioning catheter (120) yet still providing an atraumatic distal end. Furthermore, as shown in FIG. 7, each spine (204) can be configured as having a rounded shape at its distal end to provide for a blunt contact surface.

III. EXEMPLARY CATHETER END EFFECTOR WITH JOINT CONFIGURATION

FIGS. 8-11 depict another exemplary end effector (300) for a catheter such as catheter (120). For instance, catheter assembly (100) may be modified in other versions such that catheter (120) connects with end effector (300) instead of end effector (200) described above. Therefore, it should be understood that the discussion above pertaining to FIG. 1 applies to catheter assembly (100) whether catheter (120) is configured with end effector (200) or end effector (300).

Figure 8:
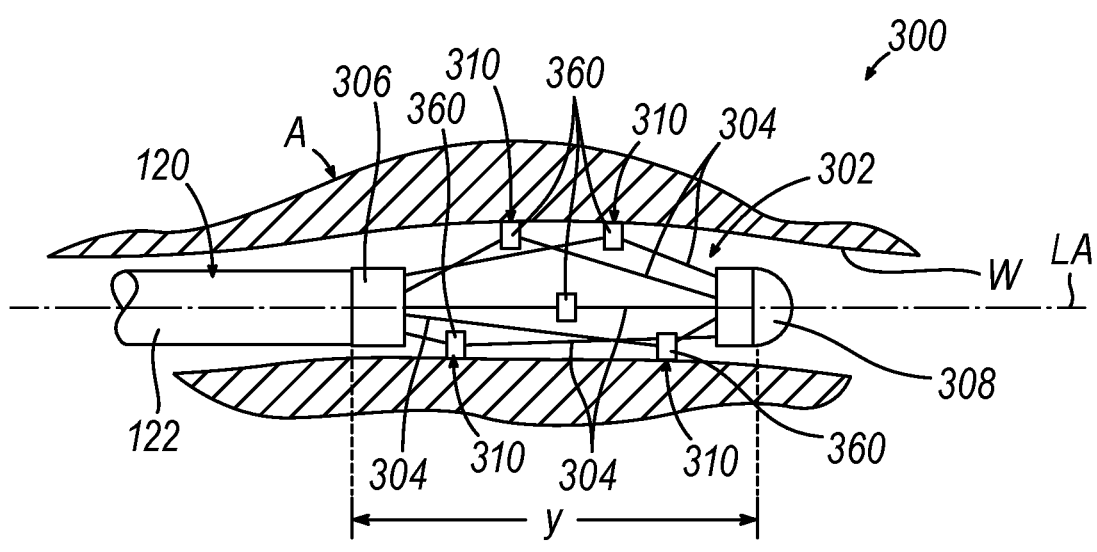
FIG. 8 depicts a side view of another exemplary catheter assembly, showing an end effector of the catheter in a deployed position.
Figure 9:
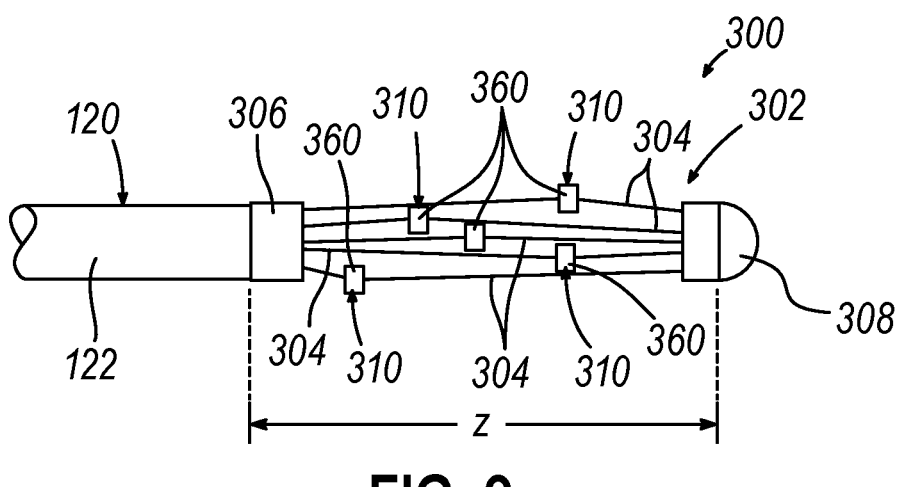
FIG. 9 depicts a side view of the catheter of FIG. 8, with the catheter in a pre-deployed position.
Figure 10:
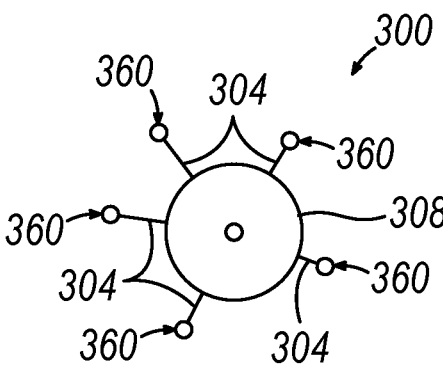
FIG. 10 depicts an end view of the catheter of FIG. 8.

As shown in FIGS. 8-10, catheter (120) is configured with end effector (300) such that end effector (300) extends longitudinally distally from catheter body (122). End effector (300) includes a spine assembly (302) having a plurality of spines (304). Each spine (304) includes a proximal end and a distal end. End effector further includes a base (306) and a tip (308). Base (306) connects with the distal end of catheter body (122). Spines (304) extend longitudinally from catheter body (122), and more specifically from base (306) of end effector (300). Spines (304) connect with tip (308) at their distal ends. Tip (308) is configured to be atraumatic, and in the present version is rounded and blunt. As mentioned above, catheter body (122) defines longitudinal axis (LA).

In comparing FIGS. 8 and 9, spines (304) are configured to adopt a first state that is associated with a pre-deployment position as shown in FIG. 9. Spines (304) are further configured to adopt a second state that is associated with a deployed position as shown in FIG. 8. In the pre-deployment position, spine assembly (302) forms a cylindrical shape defining a first circumference. In at least some versions, the first circumference generally matches the circumference at base (306) and tip (308). In the deployed position, spine assembly (302) forms an expanded basket shape defining a second circumference. As seen in FIG. 8, the second circumference is larger than the first circumference at their respective greatest dimensions. Instead of, or in addition to comparing circumference, a similar comparison can be made based upon diameters defined by spine assembly (302) in the pre-deployment position versus the deployed position. For instance, spine assembly (302) defines a smaller diameter in its pre-deployment position compared to in its deployed position.

Another way to describe spine assembly (302) and its pre-deployment and deployed positions is in terms of deflection. For instance, in the pre-deployment position of FIG. 9, spines (304) of spine assembly (302) are undeflected from longitudinal axis (LA), whereas in the deployed position of FIG. 8, spines (304) of spine assembly (302) are deflected outward from longitudinal axis (LA). In one example where spines (304) have a fixed length, in the pre-deployment position spine assembly (302) defines a length shown as (Z) in FIG. 9. In the deployed position, spine assembly (302) defines a length shown as (Y) in FIG. 8. Furthermore, comparing length (Z) and length (Y) shows that in the pre-deployment position, spine assembly (302) has a greater length than when spine assembly (302) is in the deployed position.

In terms of controlling the states of end effector (300) and the positions of spine assembly (302), in one version, spines (304) of end effector (300) are resiliently biased to expand outward from longitudinal axis (LA) defined by catheter body (122) and this resilient bias is temperature dependent.

Accordingly, end effector (300) must reach a certain temperature before it will adopt an expanded or deflected state as shown in FIG. 8. For example, end effector (300) may remain undeflected or contracted when end effector (300) is at room temperature or about 70 degrees Fahrenheit, while end effector (300) may adopt the expanded or deflected state when end effector (300) is at a higher temperature, e.g., above about 85 degrees Fahrenheit, or at body temperature or about 99 degrees Fahrenheit.

In other versions, the resilient bias of spine assembly (302) of end effector (300) is not required to be temperature dependent. For instance, introducer tool (130), which may also be considered a sheath, may be used with catheter (120) configured with end effector (300). When introducer tool surrounds or encumbers end effector (300), spine assembly (302) is contracted inward toward longitudinal axis (LA) and held in that state until introducer tool (130) is removed. Upon either retraction of introducer tool (130) or advancement of catheter (120) distal relative to introducer tool (130), end effector (300) and associated spine assembly (302) becomes unencumbered or unbound by introducer tool (130). This action allows spine assembly (302) to adopt its expanded or deflected state to which it is resiliently biased to adopt when otherwise unrestricted.

In other versions, spines (304) of spine assembly (302) may or may not be resiliently biased. For instance, catheter (120) can be configured with a translatable member that controls the position of tip (308) relative to base (306) and can be moved from an extended position to a retracted position. In doing so, spine assembly (302) is moved from its pre-deployment position to its deployed position. In one version where spines (304) are resiliently biased to their expanded state, when the translatable member is not under tension or otherwise not extended, spine assembly (302) is free to move to its neutral or home position, which coincides with the expanded state of FIG. 8 based on the resilient bias. In such a version, spine assembly (302) is moved to its contracted state or pre-deployment position by extending the translatable member distally. In some instances, the translatable member is one or more of spines (304), but in other versions the translatable member may be separate from spines (304).

In some versions where spines (304) may or may not be resiliently biased, to achieve consistent shapes adopted by spines (304) when moving from the pre-deployment position to the deployed position, spines (304) are configured with elbows or joints (310) such that spines (304) consistently bend when changing positions. In some versions, elbows or joints (310) can be shaped-in, e.g., by using shape memory alloy materials such as nitinol or other suitable materials that will be apparent to those skilled in the art in view of the teachings herein. In some versions, elbows or joints (310) may be represented as mechanical joints, i.e., where spines (304) may be joined of multiple pieces by a joint connection. In either or other approaches, elbows or joints (310) are configured to bend outwardly from longitudinal axis (LA) when spines (304) move from the pre-deployment position or first state to the deployed position or second state. Elbows or joints (310) are further configured to contract inwardly toward longitudinal axis (LA) when spines (304) move from the deployed position or second state to the pre-deployment position or first state. In the illustrated version of FIG. 8, each spine (304) is configured with one elbow or joint (310). In other versions, each spine (304) can be configured with more than one elbow or joint (310).

Irrespective of the mode used to move spine assembly (302) from its pre-deployment position to its deployed position, in the deployed position or expanded state, portions of spines (304) of end effector (300) are configured to contact interior wall (W) of a tubular vessel such as artery (A) of FIGS. 2 and 8. This contact allows for end effector (300) to be used with ablation procedures as will be described further below.

Spine assembly (302) of end effector (300) includes a plurality of electrodes (360) configured to apply RF energy and thereby ablate tissue. Some versions of electrodes (360) are configured to apply monopolar RF energy to tissue; while other versions of electrodes (360) are configured to apply bipolar RF energy to tissue. In the illustrated version, each electrode (360) connects with one of spines (304). Furthermore, each electrode (360) of its respective spine (304) connects with respective spines (304) at the bend or elbow or joint (310). In this manner, as spine (304) moves to its deployed position, electrode (360) will contact interior wall (W) of artery (A), which provides for the contact for ablation once RF energy is transmitted to electrode (360). In the illustrated version of FIG. 8, each spine (304) is configured with one elbow or joint (310) and one electrode (360) at or near elbow or joint (310). In other versions as mentioned above, spines (304) can be configured with more than one elbow or joint (310) and similarly more than one electrode (360) such that each elbow or joint (310) of respective spines (304) includes electrodes (360).

Still referring to FIGS. 8 and 9, electrodes (360) are spaced longitudinally such that they are staggered from proximal end of end effector (300) to distal end. Moreover, in some versions, electrodes (360) are evenly spaced longitudinally such that the space between adjacent electrodes (360) is consistent. However, in some other versions, electrodes (360) are irregularly spaced longitudinally where the spaces between adjacent electrodes (360) varies. In seen in FIGS. 8 and 9, in one version each electrode (360) of a plurality of electrodes (360) extends distally to different lengths in an ascending order where each electrode (360) is located further distally than its immediately proximally adjacent electrode (360). In addition to electrode spacing longitudinally, spines (304) of spine assembly (302) are arranged in a circular pattern with longitudinal axis (LA) as a common center or central apex when catheter (120) is not otherwise articulated. FIG. 10 illustrates this with spines (304) in a deployed position. This combination of longitudinally spacing electrodes (360) and circular arrangement of spines (304) provides that electrodes (360) define a helical array. This can be the case when spine assembly (302) is in the pre-deployment position and the deployed position. With the helical array an extended or lengthened circumferential ablation pattern is achieved in use.

In one example catheter (120), the circumferential ablation is achieved over a length from approximately or about 1.0 to approximately or about 1.5 centimeters. Additionally, catheter (120), in some versions, is configured to fit within arteries having diameters from approximately or about 1.5 to approximately or about 1.8 millimeters. By way of example only, and not limitation, a diameter for catheter (120) is approximately or about 1.25 millimeters. In view of the teachings herein, other sizes for catheter (120) and configurations for spines (304) and associated electrodes (360) to achieve other ablation patterns will be apparent to those skilled in the art.

Figure 11:
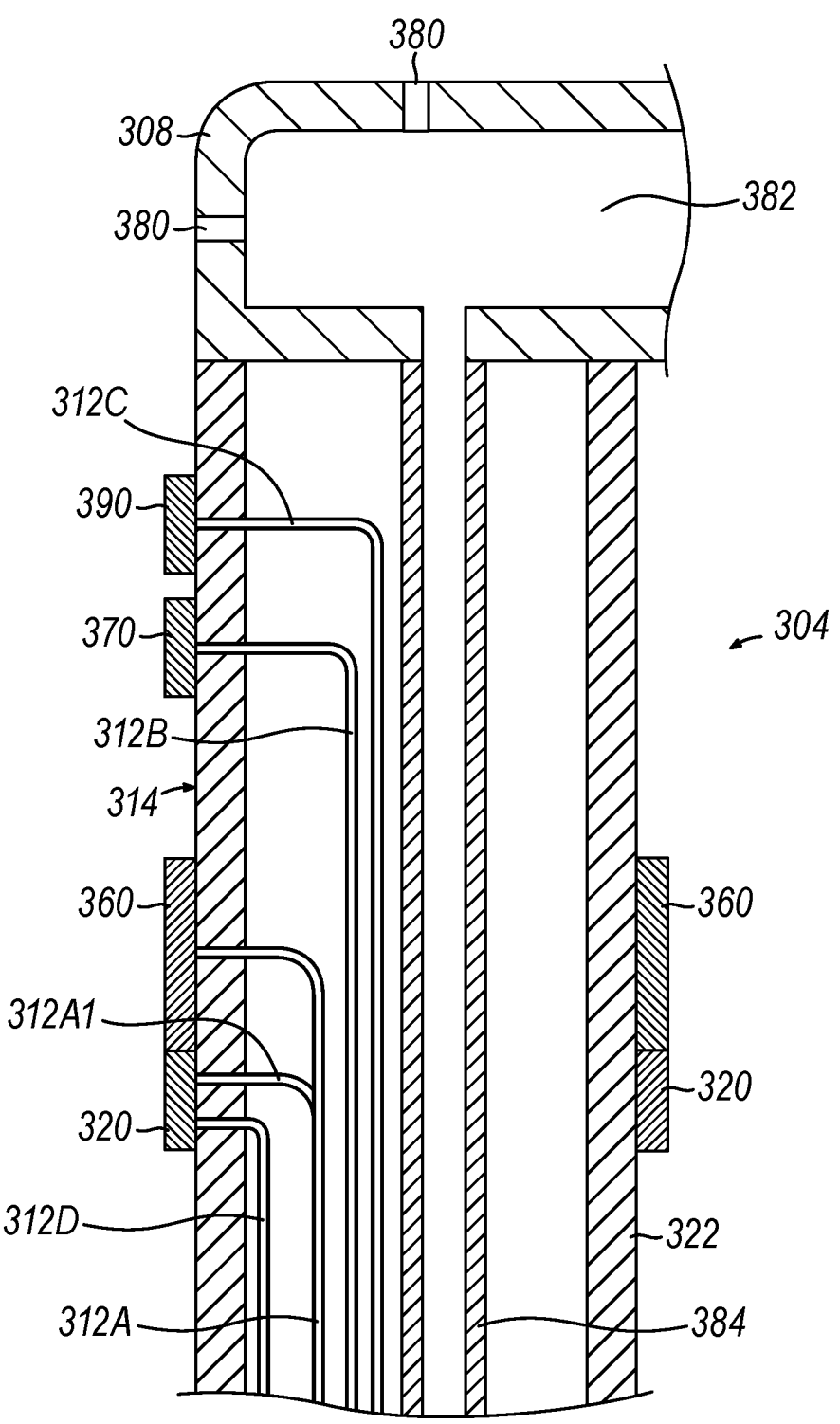
FIG. 11 depicts a partial side view in a longitudinal cross section of one of the spines of the catheter of FIG. 9.

Referring to FIG. 11, electrodes (360) in the illustrated version are configured as ring electrodes. In this manner, electrodes (360) extend continuously around its respective spine (304). This configuration promotes contact of electrodes (360) with interior wall (W) of artery (A) without a specific point location along the perimeter of spine (304) needing to be positioned in direct contact with interior wall (W). Still yet, in other versions other style electrodes may be used instead of or in addition to ring electrodes. In view of the teachings herein, other arrangements and styles or configurations for electrodes (360) will be apparent to those skilled in the art.

As shown in FIG. 11, each electrode (360) connects with a lead wire (312A) that is a conductor configured to transmit RF energy to electrode (360) for ablating tissue. Lead wire (312A) can connect with its respective electrode (360) at a terminal connection configured with electrode (360) in some versions, or as a soldered connection in other versions. Lead wire (312A) extends proximally through a lumen in catheter (120) and exiting catheter assembly (100) to ultimately connect with guidance and drive system (10), which includes an RF energy source for ablation procedures.

Spine assembly (302) of end effector (300) also includes a plurality of temperature sensors (320), with each spine (304) having at least one temperature sensor (320). In some versions each temperature sensor (320) of spines (304) is located near or contacting electrodes (360) of each respective spine. For instance, as seen in FIG. 11, temperature sensor (320) contacts electrode (360). In this configuration, temperature sensor (320) is configured to measure and transmit the temperature at or near electrode (360). With electrode (360) being configured to contact the artery wall (W) or other tissue, physician (PH) can use temperature sensor (320) to know the temperature that electrode (360) is generating at the ablation site.

In some versions, temperature sensor (320) may include a thermocouple or thermistor. In the depicted embodiment of FIG. 11, a thermocouple is formed by a portion (312A1) of lead wire (312A) and a constantan wire (312D). Wires (312A1, 312D) are electrically isolated from each other except at their distal ends where they are twisted together, covered with a short thin piece of plastic tubing, e.g., polyamide, and covered with epoxy with good thermal conductive coefficient. Wires (312A1) connects with the rest of lead wire (312A) and wires (312A, 312D) extend through the central lumen of the catheter body (122), and then extend out through the control handle (110) and to a connector (not shown) connectable to a temperature monitor (not shown). Alternatively, the temperature sensing means may be a thermistor. A suitable thermistor for use in the present invention is Model No. AB6N2-GC14KA143E/37C sold by Thermometrics (New Jersey).

Still referring to FIG. 11, spines (304) of end effector (300) are at least partially covered by a nonconductive material (322). In some versions, nonconductive material (322) completely covers spines (304) except for electrode (360). Nonconductive material is a thermoplastic in some instances, and other nonconductive materials that may be used will be apparent to those skilled in the art in view of the teachings herein.

End effector (300) of catheter (120) is further configured with irrigating features (380). For example, as shown in FIG. 11, exemplary irrigating features (380) are located in tip (308) of end effector (300). As shown, tip (308) has multiple irrigating features (380), with at least one at the distal-most end and another at least one on an outward facing distal portion of tip (308). In some other versions, irrigating features (380) can instead or also be located near electrodes (360) to provide cooling to the ablation site. Referring to FIG. 11, irrigating features (380) connect with a fluid chamber (382) within a tip (308). Fluid chamber (382) further connects with an irrigation tube (384) that ultimately is connectable with fluid conduit (40) and fluid source (42) as mentioned above with respect to FIG. 1. As noted above, such irrigation features may be omitted in some versions.

End effector (300) of catheter (120) is further configured with various other sensors. Referring to FIG. 11, each spine (304) of spine assembly (302) includes a position sensor (370) and a force sensor (390). As mentioned above, position sensors (370) are configured to communicate the position of end effector (300) relative to anatomical features within patient (PA). Force sensors (390) are configured to provide feedback to physician (PH) so that physician (PH) can avoid exceeding forces that may cause unintended puncture of arteries or other tissues of patient (PA). Referring to FIG. 11, position sensors (370) and force sensors (390) of spines (304) connect with respective lead wires (312B, 312C) within spine (304). Lead wires (312B, 312C) extend through a lumen of catheter (120) and ultimately connect with cable (30), which couples catheter assembly (100) with guidance and drive system (10) as mentioned above. In the present examples of FIG. 11, position sensors (370) and force sensors (390) of spines (304) are located on an outward facing surface (314) of spines (304). However, in other versions, position or force sensors (370, 390) can be located on other surfaces of spines (304), and such positioning will be apparent to those skilled in the art in view of the teachings herein.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A catheter for use in a medical procedure includes a catheter body defining a longitudinal axis. The catheter also includes a spine assembly connected with the catheter body at a distal end. The spine assembly includes (i) a plurality of spines, each spine having a distal end, each spine extending distally with at least two of the spines extending distally to different lengths, (ii) a plurality of electrodes configured to ablate tissue, each electrode being connected with one of the spines, and (iii) a plurality of temperature sensors, each temperature sensor being connected with one of the spines.

Example 2

The catheter of Example 1, each spine extending distally to different lengths.

Example 3

The catheter of any one or more of Examples 1 through 2, each electrode being located at the distal end of each respective spine.

Example 4

The catheter of any one or more of Examples 1 through 3, each temperature sensor being located at the distal end of each respective spine.

Example 5

The catheter of any one or more of Examples 1 through 4, the distal end of each spine being rounded to provide a blunt contact surface.

Example 6

The catheter of any one or more of Examples 1 through 5, each spine of the plurality of spines extending from a central apex of the spine assembly.

Example 7

The catheter of any one or more of Examples 1 through 6, each spine extending distally to different lengths in an ascending order.

Example 8

The catheter of any one or more of Examples 1 through 7, each spine of the plurality of spines being made of nitinol.

Example 9

The catheter of any one or more of Examples 1 through 8, the plurality of spines being configured to expand outwardly to contact an interior wall of a tubular vessel.

Example 10

The catheter of any one or more of Examples 1 through 9, the plurality of spines being resiliently biased toward an expanded state.

Example 11

The catheter Example 10, the resilient bias of the plurality of spines being temperature dependent such that at a first temperature the plurality of spines is configured to adopt the expanded state, and at a second temperature the plurality of spines is configured to adopt a contracted state.

Example 12

The catheter of any one or more of Examples 1 through 11, each temperature sensor including a thermocouple.

Example 13

The catheter of any one or more of Examples 1 through 12, with one or more of the plurality of electrodes including a ring electrode.

Example 14

The catheter of any one or more of Examples 1 through 12, with one or more of the plurality of electrodes including a deep drawn cup electrode.

Example 15

The catheter of any one or more of Examples 1 through 14, further including a position sensor.

Example 16

The catheter of any one or more of Examples 1 through 15, further including an irrigating feature configured to deliver cooling fluid.

Example 17

The catheter of any one or more of Examples 1 through 16, further including a force sensor.

Example 18

The catheter of any one or more of Examples 1 through 17, the catheter being configured to articulate.

Example 19

The catheter of any one or more of Examples 1 through 18, further including a conductor connected with one of the plurality of electrodes, the conductor being configured to transmit RF energy to the electrode.

Example 20

The catheter of any one or more of Examples 1 through 19, each electrode of the plurality of electrodes being connected with one of the temperature sensors of the plurality of temperature sensors.

Example 21

The catheter of Example 20, each electrode of the plurality of electrodes being connected with one of the temperature sensors of the plurality of temperature sensors by sharing the conductor.

Example 22

The catheter of any one or more of Examples 1 through 21, the plurality of spines at least partially being covered by a nonconductive material.

Example 23

The catheter of Example 22, the nonconductive material being thermoplastic.

Example 24

The catheter of any one or more of Examples 1 through 23, a proximal end of the catheter body having greater stiffness than the distal end to allow for positioning the catheter while being atraumatic at the distal end.

Example 25

The catheter of any one or more of Examples 1 through 24, the plurality of electrodes being longitudinally staggered.

Example 26

The catheter of any one or more of Examples 1 through 25, the plurality of electrodes being irregularly spaced longitudinally.

Example 27

The catheter of any one or more of Examples 1 through 26, the plurality of electrodes defining a helical array.

Example 28

An apparatus for use in a medical procedure includes a catheter having a catheter body defining a longitudinal axis. The apparatus also includes a spine assembly connected with the catheter body at a distal end. The spine assembly includes: (i) a plurality of spines, each spine having a distal end, each spine extending distally with at least two of the spines extending distally to different lengths, the plurality of spines being biased toward an expanded position when unencumbered, (ii) a plurality of electrodes configured to ablate tissue, each electrode being connected with one of the spines, and (iii) a plurality of temperature sensors, each temperature sensor being connected with one of the spines. The apparatus also includes an introducer member configured to selectively slide over the spine assembly to cause the plurality of spines to adopt a contracted position when the introducer member is positioned over the spine assembly, and to permit the plurality of spines to adopt the expanded position when the introducer member is not positioned over the spine assembly.

Example 29

A catheter for use in a medical procedure includes a catheter body defining a longitudinal axis, and a spine assembly connected with the catheter body at a distal end. The spine assembly includes a plurality of spines, each spine having a proximal end and a distal end, the proximal end of each of the plurality of spines connecting with the catheter body, the plurality of spines being configured to adopt a first state associated with a pre-deployment position, the plurality of spines further being configured to adopt a second state associated with a deployed position. The spine assembly further includes a tip connected with the distal end of each of the plurality of spines, the tip being configured to be atraumatic, a plurality of electrodes configured to ablate tissue, each electrode being connected with one of the spines, and a plurality of temperature sensors, each temperature sensor being connected with one of the spines.

Example 30

The catheter of Example 29, the plurality of spines defining a basket structure.

Example 31

The catheter of any one or more of Examples 29 through 30, the pre-deployment position having the plurality of spines undeflected, and the deployment position having the plurality of spines deflected.

Example 32

The catheter of any one or more of Examples 29 through 31, the plurality of spines in the first state having a smaller circumference than the plurality of spines in the second state.

Example 33

The catheter of any one or more of Examples 29 through 32, the plurality of spines comprising nitinol.

Example 34

The catheter of any one or more of Examples 29 through 33, the plurality of electrodes being longitudinally staggered.

Example 35

The catheter of any one or more of Examples 29 through 34, the plurality of electrodes being irregularly spaced longitudinally.

Example 36

The catheter of any one or more of Examples 29 through 35, the plurality of electrodes defining a helical array.

Example 37

The catheter of any one or more of Examples 29 through 36, the plurality of spines each including an elbow configured to bend outwardly from the longitudinal axis when the plurality of spines moves from the first state associated with the pre-deployment position to the second state associated with the deployed position. The elbow is configured to contract inwardly toward the longitudinal axis when the plurality of spines moves from the second state associated with the deployed position to the first state associated with the pre-deployment position.

Example 38

The catheter of Example 37, each of the elbows having one of the plurality of electrodes located thereon.

Example 39

The catheter of any one or more of Examples 29 through 38, the plurality of electrodes being configured to contact an interior wall of a vessel when the plurality of spines is in the second state associated with the deployed position.

Example 40

The catheter of any one or more of Examples 37 through 39, the plurality of spines each including more than one elbow.

Example 41

The catheter of any one or more of Examples 29 through 40, the spine assembly comprising a translatable member connected with the tip, the translatable member being configured to translate longitudinally to actuate the plurality of spines from the first state associated with the pre-deployment position to the second state associated with the deployed position.

Example 42

The catheter of Example 41, the tip being configured to translate longitudinally in unison with the translatable member.

Example 43

The catheter of any one or more of Examples 41 through 42, the translatable member being translatable relative to the catheter body.

Example 44

The catheter of any one or more of Examples 41 through 43, the translatable member being translatable proximally to move the plurality of spines from the first state associated with the pre-deployment position to the second state associated with the deployed position.

Example 45

The catheter of any one or more of Examples 29 through 44, the catheter body being translatable longitudinally relative to a sheath configured to selectively cover or uncover the spine assembly with the sheath.

Example 46

The catheter of any one or more of Examples 29 through 45, each electrode of the plurality of electrodes extending distally to different lengths in an ascending order.

Example 47

The catheter of any one or more of Examples 29 through 46, the plurality of spines being resiliently biased toward the second state associated with the deployed position.

Example 48

The catheter of any Example 47, the resilient bias of the plurality of spines being temperature dependent such that at a first temperature the plurality of spines is configured to adopt the pre-deployment position, and at a second temperature the plurality of spines is configured to adopt the deployed position.

Example 49

The catheter of any one or more of Examples 29 through 48, each temperature sensor including a thermocouple.

Example 50

The catheter of any one or more of Examples 29 through 49, with one or more of the plurality of electrodes comprising a ring electrode.

Example 51

The catheter of any one or more of Examples 29 through 50, further including a position sensor.

Example 52

The catheter of any one or more of Examples 29 through 51, further including an irrigating feature configured to deliver cooling fluid.

Example 53

The catheter of any one or more of Examples 29 through 52, further including a force sensor.

Example 54

The catheter of any one or more of Examples 29 through 53, the catheter being configured to articulate.

Example 55

The catheter of any one or more of Examples 29 through 54, each electrode of the plurality of electrodes being connected with a conductor, the conductor being configured to transmit RF energy to the electrode.

Example 56

The catheter of any one or more of Examples 29 through 55, each electrode of the plurality of electrodes being connected with one of the temperature sensors of the plurality of temperature sensors.

Example 57

The catheter of any one or more of Examples 29 through 56, each electrode of the plurality of electrodes being connected with one of the temperature sensors of the plurality of temperature sensors by sharing the conductor.

Example 58

The catheter of any one or more of Examples 29 through 57, the plurality of spines at least partially being covered by a nonconductive material.

Example 59

The catheter of Example 58, the nonconductive material being thermoplastic.

Example 60

The catheter of any one or more of Examples 29 through 59, a proximal end of the catheter body having greater stiffness than the distal end to allow for positioning the catheter while being atraumatic at the distal end.

V. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A catheter for use in a medical procedure comprising:
   (a) a catheter body defining a longitudinal axis, the catheter body having a distal end; and
   (b) a spine assembly connected with the distal end of the catheter body, the spine assembly configured to assume a pre-deployment position defining a first circumference and a first length and a deployment position defining a second circumference greater than the first circumference and a second length lesser than the first length, the spine assembly comprising:
      (i) a distal tip;
      (ii) a proximal base;
      (iii) a plurality of spines arranged in a generally circular pattern around a longitudinal axis of the spine assembly, each spine of the plurality of spines having a proximal end extending from the proximal base, a distal end connected to the distal tip, and a joint between the proximal end and the distal end, the joint of each spine configured to deflect outwardly when the spine assembly is in the deployment position, and all of the joints on the plurality of spines being at different and unique longitudinal distances relative to each other from the proximal base such that when the spine assembly is in the deployment position all of the joints on the plurality of spines deflect outwardly at different and unique longitudinal positions relative to each other along the second length of the spine assembly, and
      (iv) a plurality of electrodes configured to contact and ablate an interior wall of a tubular vessel, each electrode of the plurality of electrodes being connected with a respective spine of the plurality of spines at or near the respective joint, the plurality of electrodes being staggered from the proximal base to the distal tip such that each electrode of a different spine is at a different and unique longitudinal distance from the proximal base along its respective spine and such that the plurality of electrodes defines a generally helical electrode array around the generally circular pattern of the plurality of spines.

2. The catheter of claim 1, further comprising a conductor connected with at least one of the plurality of electrodes, the conductor being configured to transmit RF energy to the at least one of the plurality of electrodes.

3. The catheter of claim 1, wherein the spines are configured to bend outwardly at their respective joints when the spine assembly is moved from the pre-deployment position to the deployment position and to contract inwardly at their respective joints when the spine assembly is moved from the deployment position to the pre-deployment position.

4. The catheter of claim 1, further comprising a plurality of temperature sensors, each temperature sensor of the plurality of temperature sensors being connected with a respective spine.

5. The catheter of claim 1, further comprising a plurality of position sensors, each position sensor of the plurality of position sensors being connected with a respective spine.

6. The catheter of claim 1, further comprising a plurality of force sensors, each force sensor of the plurality of force sensors being connected with a respective spine.

7. The catheter of claim 1, wherein the electrodes are evenly staggered longitudinally such that a longitudinal separation space between adjacent electrodes on their respective spines is consistent.

8. The catheter of claim 1, wherein the electrodes are irregularly staggered longitudinally such that a longitudinal separation space between adjacent electrodes on their respective spines is inconsistent.

9. The catheter of claim 1, wherein assumption of the pre-deployment position and the deployment position by the spine assembly depends on a temperature of the spine assembly.

10. The catheter of claim 1, wherein the spine assembly assumes the deployment position when the temperature of the spine assembly is above 85 degrees Fahrenheit.

11. The catheter of claim 1, wherein the spine assembly assumes the deployment position when the temperature of the spine assembly is at about 99 degrees Fahrenheit.

12. The catheter of claim 1, further comprising a translatable member movable from a first position in which the spine assembly is in the pre-deployment position to a second position in which the spine assembly is in the deployment position.

13. The catheter of claim 12, wherein the translatable member comprises one of the spines.

14. The catheter of claim 1, wherein the spines are resiliently biased to deflect outwardly.

15. The catheter of claim 1, wherein the joints include shape-memory.

16. The catheter of claim 1, wherein the electrodes are configured to apply monopolar RF energy.

17. The catheter of claim 1, wherein the electrodes are configured to apply bipolar RF energy.

18. The catheter of claim 1, wherein the tubular vessel has a diameter from approximately or about 1.5 mm to approximately or about 1.8 mm.

* * * * *